(12) United States Patent
Meshram et al.

(10) Patent No.: US 8,202,989 B2
(45) Date of Patent: Jun. 19, 2012

(54) **ONE STEP PROCESS FOR THE PREPARATION OF SUBSTITUTED 5, 10-DIHYDRODIBENZO [*B,E*][1, 4]DIAZEPINE-11-ONES**

(75) Inventors: Harshadas Mitaram Meshram, Hyderabad (IN); Palakuri Ramesh Goud, Hyderabad (IN); Bandi Chennakesava Reddy, Hyderabad (IN); Jhillu Singh Yadav, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 218 days.

(21) Appl. No.: 12/684,710

(22) Filed: Jan. 8, 2010

(65) Prior Publication Data

US 2010/0228023 A1 Sep. 9, 2010

(30) Foreign Application Priority Data

Jan. 12, 2009 (IN) ............... 46/DEL/2009

(51) Int. Cl.
*C07D 243/10* (2006.01)
*C07D 243/38* (2006.01)

(52) U.S. Cl. ...................................... 540/456
(58) Field of Classification Search ............ 540/495
See application file for complete search history.

(56) References Cited

FOREIGN PATENT DOCUMENTS

WO WO 2006/097449 A1 9/2006

OTHER PUBLICATIONS

Breslin et al. (J. Med. Chem. (1995), 38, 771-793).*
Becalli et al., "Palladium-mediated approach to dibenzo[*b,e*][1,4]diazepines and benzopyrido-analogues. An efficient synthesis of tarpane," *Tetrahedron 61*: 61-68, 2005.
Hanze et al., "Dibenzo[*b,e*][1,4]diazepines," *J. Med. Chem 6*: 767-771, Nov. 1963.

* cited by examiner

*Primary Examiner* — Bruck Kifle
(74) *Attorney, Agent, or Firm* — Seed IP Law Group PLLC

(57) ABSTRACT

The present invention provides one step processes for the preparation of substituted dibenzo[b,e][1,4]-diazepine-11-ones by the reaction of substituted isatoic anhydrides with substituted 1,2-phenylenediamines in the presence of aqueous acetic acid.

14 Claims, No Drawings

ONE STEP PROCESS FOR THE PREPARATION OF SUBSTITUTED 5, 10-DIHYDRODIBENZO [B,E][1,4]DIAZEPINE-11-ONES

CROSS REFERENCE TO RELATED APPLICATION

This application claims the benefit under 35 U.S.C. §119 (b) of Indian Patent Application No. 0046/DEL/2009, filed Jan. 12, 2009, which application is incorporated herein by reference in its entirety.

FIELD OF THE INVENTION

The present invention relates to a one step process for the preparation of substituted dihydrodibenzo[b,e][1,4]diazepine-11-one derivatives.

BACKGROUND OF THE INVENTION

Dibenzo[b,e][1,4]diazepine-11-ones are useful intermediates in pharmaceuticals. Particularly, dibenzo[b,e][1,4]diazepine-11-ones are active as an antidepressant, antitumor and anticonvulsant agents. Dibenzo[b,e][1,4]diazepin-11-ones also serve as intermediates for the preparation of dibenzo[1,4]diazepines.

The known processes for preparing dibenzo[b,e][1,4]diazepine-1'-ones are based on the condensation of amino and halo compounds followed by the cyclization using palladium salts, which involves a number of steps.

Reference may be made to PCT Published Patent Application No. WO 2006/097449 wherein the dibenzo[b,e][1,4]diazepine-11-one ring is prepared by the condensation of anthranilic acid and o-bromo nitrobenzene in the presence of copper powder at 140° C. to obtain an intermediate which upon reduction, followed by cyclization, gives diazepine-one. The main drawback of this process is the use of amino and halo compounds which are not commercially available and that it involves more number of steps. Moreover, the cyclization step requires expensive palladium catalyst.

Another reference may be made to E. M. Beccalli et al., *Tetrahedron* (2005), Vol. 61, pp. 61-68, wherein the condensation of o-nitrobenzoyl chloride with o-iodoaniline gives an intermediate which upon intramolecular amination with palladium acetate and BINAP gives dibenzo[1,4]dazepin-11-one. Particularly, this method has a disadvantage of using hazardous benzoyl chloride and rarely available iodoaniline. Another drawback is the use of expensive palladium salt and BINAP as a catalyst. Moreover, the use of anhydrous toluene and extended reaction time (24 hrs), make the procedure inconvenient.

Yet another reference may be made to A. R. Hanze et al., *J. Med. Chem.* (1963), pp. 767-771, wherein dibenzo[b,e][1,4]diazepine-11-ones are prepared starting from anthranilic acid and o-bromonitrobenzene at 200° C. using n-amyl alcohol as a medium. The intermediate was then cyclized by heating at 250° C. This process has the drawback of using expensive amyl alcohol and higher temperature, which is very difficult to maintain on a large scale.

All the earlier reported processes involve more number of steps and use hazardous starting materials, carcinogenic hydrocarbon as a solvent, which is difficult to handle on large scale and also generate waste effluent. Moreover, palladium catalyst and BINAP are reported for cyclizations which are very expensive and have negative influence on the economy. In addition to this, the reactions require higher temperature (200-250° C.) which is very inconvenient on a large scale production. Although practical in the laboratory, all these methods have following disadvantages on a commercial scale.

1. Numbers of steps involved are more.
2. Use of hazardous and corrosive starting halides or acid chlorides.
3. Expensive reagents are used for cyclization.
4. Use of hydrocarbon solvent as a medium.
5. Higher temperature required for reaction.
6. Generates metal containing waste.

There exists therefore a need to provide a one step process for the preparation of substituted dihydrodibenzo[b,e][1,4]diazepine-11-ones which does not have the above-described disadvantages.

SUMMARY OF THE INVENTION

The present invention provides a one step process for the preparation of substituted dibenzo[b,e][1,4]diazepine-11-ones by the reaction of substituted isatoic anhydrides with substituted 1,2-phenylenediamines in the presence of aqueous acetic acid. The present invention reduces the number of steps into one step thereby avoiding the use of number of chemicals. The present invention also avoids the use of organic solvents and expensive reagents. In addition to these advantages, the reaction can be carried out at lower temperature. The present invention may therefore be useful in the pharmaceutical production of substituted dibenzo[b,e][1,4]diazepine-11-ones where the possibility of any metal ion contamination may be avoided.

Accordingly, the main object of the present invention is to provide a one step process for the preparation of substituted dibenzo[b,e][1,4]diazepine-11-ones.

Another object of the present invention is to carry out the condensation and cyclization in one step using aqueous acetic acid.

Yet another object of the present invention is to develop a process for the preparation of substituted dibenzo[b,e][1,4]diazepine-11-ones without the use of hazardous chemicals.

Yet another object of the invention is to avoid the use of expensive reagents for cyclization.

Yet another objective of the invention is to avoid the use of hydrocarbon as a solvent.

Yet another object of the invention is to avoid the generation of metal containing waste.

Yet another objective of the present invention is to reduce the use of chemicals.

Yet another object of the invention is to perform the reaction in shorter time.

Yet another object of the invention is to carry out the reaction at moderate temperature.

Yet another object of the invention is to provide a general process which may be applicable for substituted o-phenylenediamines and substituted isatoic anhydrides.

Still another object of the present invention is to provide a metal ion free process, which avoids the possibility of contamination of metal ion in the pharmaceutical products.

DETAILED DESCRIPTION OF THE INVENTION

Accordingly the present invention provides a single step process for the preparation of substituted dibenzo[b,e][1,4]diazepine-1'-ones which comprises reacting a substituted 1,2-phenylenediamine of formula (1):

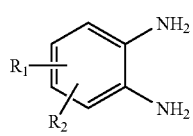

wherein substituents $R_1$ and $R_2$ are selected from the group consisting of hydrogen, halogen, alkyl, alkoxy and nitro, with an isatoic anhydride of formula (2):

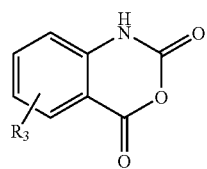

wherein substituent $R_3$ is selected from the group consisting of hydrogen, halogen, alkyl, alkoxy and nitro, in the presence of aqueous acetic acid, at a temperature in the range of 70-150° C. for a period of 1-5 hrs, pouring the resultant reaction mixture into ice cold water and isolating the resultant solid product by neutralization, followed by filtration to obtain the desired substituted dibenzo[b,e][1,4]diazepine-11-one product of formula (3):

(3)

wherein $R_1$, $R_2$, and $R_3$ are selected from the group consisting of hydrogen, halogen, alkyl, alkoxy and nitro.

For purposes of this invention and unless specified to the contrary, the terms "halogen", "alkyl" and "alkoxy" are intended to have their generally accepted meanings. Preferably, the term "halogen" refers to iodo, bromo, fluoro and chloro; the term "alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl(iso-propyl), n-butyl, n-pentyl, 1,1-dimethylethyl(t-butyl), 3-methylhexyl, 2-methylhexyl, and the like, which may be optionally substituted by one or more halogens; and the term "alkoxy" refers to a radical of the —$OR_a$ where $R_a$ is an alkyl as defined above.

In an embodiment of the present invention, the substituents present on the benzene rings of the compounds of formula (1), (2) and (3) are at ortho-, meta- or para-position.

In yet another embodiment, the concentration of acetic acid used in the process is in the range of 50%-98% solution in water.

In yet another embodiment, the reaction is carried out at temperature preferably in the range of 75° C. to 85° C.

In yet another embodiment, the reaction is carried out for a time period preferably in the range of 3 to 4 hrs.

In yet another embodiment, the 1,2-phenylenediamine of formulae (1) used in the process is selected from the group consisting of 1,2-phenylenediamine, 3,4-dimethyl-1,2-phenylenediamine, methyl-1,2-phenylenediamine-4-benzoate and 4-methyl-1,2-phenylenediamine.

In yet another embodiment, the isatoic anhydride of formula (2) used in the process is selected from the group consisting of 6-fluoro isatoic anhydride, isatoic anhydride, and 6-chloro isatoic anhydride.

In yet another embodiment, the substituted dibenzo[b,e][1,4]diazepine-11-one of formula (3) obtained by the process of the invention is selected from the group consisting of 10,11-dihydro-5H-dibenzo[b,e][1,4]diazepin-1'-one; 2-fluoro-10,11-dihydro-5H-dibenzo[b,e][1,4]diazepin-11-one; 2-chloro-10,11-dihydro-5H-dibenzo[b,e][1,4]diazepin-11-one; 8,9-dimethyl-10,11-dihydro-5H-dibenzo[b,e][1,4]diazepin-11-one; methyl 11-oxo-10,11-dihydro-5H-dibenzo[b,e][1,4]diazepin-8-carboxylate and 2-chloro-8-methyl-10,11-dihydro-5H-dibenzo[b,e][1,4]diazepin-11-one.

In yet another embodiment, the yield of substituted dibenzo[b,e][1,4]diazepine-11-one of formulae (3) obtained from the process is in the range of 85%-98%.

In yet another embodiment, the process of the invention is substantially described herein as set forth individually in the following examples.

In particular, the present invention provides a process for the preparation of dibenzo[b,e][1,4]diazepine-11-one in a one step and in high yield by the reaction of substituted o-phenylenediamine with substituted isatoic anhydride in the presence of aqueous acetic acid. The main advantage of the invention is that the steps are reduced severely to one step and it also avoids the use of hazardous chemicals and metallic reagents, thereby avoiding the possibility of any contamination of metal ions in the pharmaceutical products.

To overcome the difficulties associated with earlier processes for the preparation of substituted dibenzo[b,e][1,4]-diazepine-11-one, the inventors of present invention developed a one step process for the preparation of substituted dibenzo[b,e][1,4]-diazepine-11-one. The present process is useful for the preparation of substituted dibenzo[b,e][1,4]-diazepine-11-ones by the condensation of substituted o-phenylenediamines with substituted isatoic anhydrides in the presence of dilute acetic acid. Aqueous acetic acid solutions having a concentration of 50%, 75% and 98% are suitable for quantitative yield of diazepine-one. Preferably a 70% solution gave the good results. The acetic acid serves as a solvent as well as acid catalyst. The temperature ranging from 70° C. to 150° C. is suitable for the completion of reaction, preferably at the range from 80° C. to 130° C. The reaction time ranges from 1 hr to 5 hrs to complete the reaction, preferably from 2 to 3 hrs.

The following Reaction Scheme 1 represents the process of the invention, wherein $R_1$, $R_2$ and $R_3$ are each independently selected from the group consisting of hydrogen, halogen, alkyl, alkoxy and nitro:

REACTION SCHEME 1

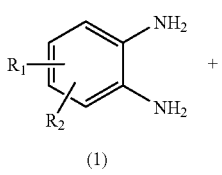

(1)

-continued

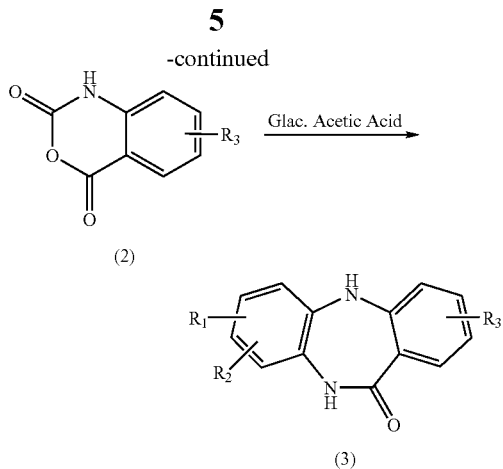

The substituted 1,2-phenylenediamines of formula (1) and the substituted isatoic anhydrides of formula (2) are commercially available or can be prepared by methods known to one skilled in the art.

The process described above provides a compound of formula (3) in one step. The condensation and subsequent cyclization occurs in situ. After standard work up, the compound of formula (3) is the only sole product. The reaction time of the process varies depending on the substituents on the compound of formula (1). The process is suitable for the reaction of ortho-, para- and meta-substituted 1,2-phenylenediamines of formula (1) as well as for substituted isatoic anhydrides of formula (2).

The process described herein for the preparation of substituted dibenzo[b,e][1,4]-diazepine-11-ones has following advantages in view of the known processes for preparing substituted dibenzo[b,e][1,4]-diazepine-11-ones.

1. The process gives substituted dibenzo[b,e][1,4]-diazepine-11-ones in one step.
2. Condensation and cyclization take place in single step.
3. Commercially available acetic acid is used as a reagent as well as medium.
4. Avoids the use of expensive reagents for cyclization
5. Avoids the use of metal catalysts and hydrocarbon solvent.
6. Applicable for substituted 1,2-phenylenediamines and substituted isatoic anhydrides.
7. Yields are very high.
8. Minimizes the use of chemicals and generation of waste.
9. Avoids the possibility of metal ion contamination in pharmaceutical Products.

The following examples are given by the way of illustration and therefore should not be construed to limit the scope of the invention.

Example 1

Synthesis of 10,11-dihydro-5H-dibenzo[b,e][1,4]diazepin-11-one

A mixture of isatoic anhydride (1 mol) and 1,2 phenylenediamine (1.1 mol) in aglacial acetic acid (60%) was heated at 75° C. for 3 hrs. The resulting mixture was diluted with water and solid filtered to obtained dibenzo[b,e][1,4]-diazepine-11-one in 96% yield.

Example 2

Synthesis of 2-fluoro-10,11-dihydro-5H-dibenzo[b,e][1,4]diazepin-1'-one

6-Fluoro isatoic anhydride and 1,2-phenylenediamine were dissolved in acetic acid (80%) and the mixture heated at 115° C. for 2 hrs. The mixture was poured in water and extracted with ethyl acetate, washed with bicarbonate solution, dried and 2-fluoro-10,11-dihydro-5H-dibenzo[b,e][1,4]diazepin-11-one was isolated (93%) by evaporation of solvent.

Example 3

Synthesis of 2-chloro-10,11-dihydro-5H-dibenzo[b,e][1,4]diazepin-11-one

6-Chloro isatoic anhydride (0.1 mol) and 1,2-phenylenediamine (0.1 mol) were dissolved in acetic acid (90%) and the mixture heated at 100° C. for 2.5 hrs. The mixture was poured into water and extracted with ethyl acetate, neutralized, dried and 2-chloro-10,11-dihydro-5H-dibenzo[b,e][1,4]diazepin-11-one was isolated (94%) after removal of solvent under reduced pressure.

Example 4

Synthesis of 8,9-dimethyl-10,11-dihydro-5H-dibenzo[b,e][1,4]diazepin-11-one 3,4-Dimethyl-1,2-phenylenediamine (0.1 mol) was dissolved in acetic acid (70%) and then isatoic anhydride (0.1 mol) was added to the solution. The resulting mixture was heated at 85° C. for 3 hrs. The mixture was poured into ice-cold water and 8,9-dimethyl-10,11-dihydro-5H-dibenzo[b,e][1,4]diazepin-11-one was isolated (97%) by neutralization and filtration.

Example 5

Synthesis of methyl 11-oxo-10,11-dihydro-5H-dibenzo[b,e][1,4]diazepin-8-carboxylate A solution of methyl-1,2-phenylenediamine-4-benzoate (0.1 mol) and isatoic anhydride (0.1 mol) in acetic acid (75%) was heated at 120° C. for 2 hrs. The mixture was diluted with water and extracted with dichloromethane, washed with water and dried over $Na_2SO_4$. Methyl 11-oxo-10,11-dihydro-5H-dibenzo[b,e][1,4]diazepin-8-carboxylate was isolated (92%) after removal of solvent under reduced pressure.

Example 6

Synthesis of 2-chloro-8-methyl-10,11-dihydro-5H-dibenzo[b,e][1,4]diazepin-11-one A mixture of 4-methyl-1,2-phenylenediamine (0.1 mol) and 6-chloro isatoic anhydride (0.1 mol) in acetic acid (85%) was heated at 110° C. for 2 hrs. The mixture was poured into ice-cold water and 2-chloro-8-methyl-10,11-dihydro-5H-dibenzo[b,e][1,4]diazepin-11-one was isolated (93%) after neutralisation and filtration.

All of the foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A process for the preparation of a compound of formula (3):

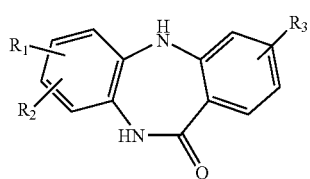
(3)

wherein $R_1$, $R_2$, and $R_3$ are selected from the group consisting of hydrogen, halogen, alkyl, alkoxy and nitro; which process comprises reacting a compound of formula (1):

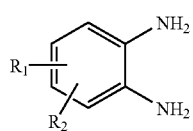
(1)

wherein substituents $R_1$ and $R_2$ are selected from the group consisting of hydrogen, halogen, alkyl, alkoxy and nitro, with a compound of formula (2):

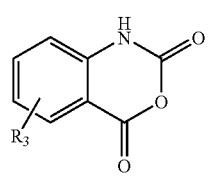
(2)

wherein substituent $R_3$ is selected from the group consisting of hydrogen, halogen, alkyl, alkoxy and nitro, in the presence of aqueous acetic acid, at a temperature in the range of 70-150° C. for a period of 1-5 hrs, pouring the resultant reaction mixture into ice cold water and isolating the resultant solid product by neutralization, followed by filtration to obtain the compound of formula (3).

2. The process of claim 1, wherein the concentration of acetic acid used is in the range of 50%-98% solution in water.

3. The process of claim 1, wherein the reaction is carried out at temperature in the range of 75° C. to 85° C.

4. The process of claim 1, wherein the reaction carried out for a time period in the range of 3 hr to 4 hrs.

5. The process of claim 1, wherein the compound of formula (1) used is selected from the group consisting of 1,2-phenylenediamine, 3,4-dimethyl-1,2-phenylenediamine, methyl-1,2-phenylenediamine-4-benzoate and 4-methyl-1,2-phenylenediamine.

6. The process of claim 1, wherein the compound of formula (2) used is selected from the group consisting of isatoic anhydride, 6-fluoro isatoic anhydride, and 6-chloro isatoic anhydride.

7. The process of claim 1 wherein the compound of formula (3) obtained is selected from the group consisting of 10,11-dihydro-5H-dibenzo[b,e][1,4]diazepin-11-one; 2-fluoro-10,11-dihydro-5H-dibenzo[b,e][1,4]diazepin-11-one; 2-chloro-10,11-dihydro-5H-dibenzo[b,e][1,4]diazepin-11-one; 8,9-dimethyl-10,11-dihydro-5H-dibenzo[b,e][1,4]diazepin-11-one; methyl 11-oxo-10,11-dihydro-5H-dibenzo[b,e][1,4]diazepin-8-carboxylate and 2-chloro-8-methyl-10,11-dihydro-5H-dibenzo[b,e][1,4]diazepin-11-one.

8. The process of claim 1, wherein the yield of the compound of formula (3) obtained is in the range of 85%-98%.

9. A one step process for the preparation of a compound of formula (3):

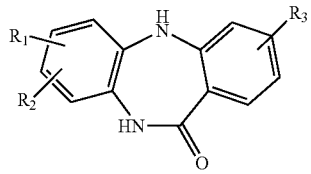
(3)

wherein $R_1$, $R_2$, and $R_3$ are selected from the group consisting of hydrogen, halogen, alkyl, alkoxy and nitro; which comprises reacting a compound of formula (1):

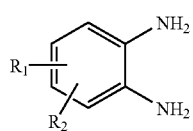
(1)

wherein substituents $R_1$ and $R_2$ are selected from the group consisting of hydrogen, halogen, alkyl, alkoxy and nitro, with a compound of formula (2):

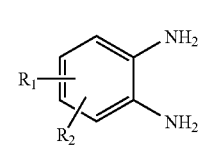
(2)

wherein substituent $R_3$ is selected from the group consisting of hydrogen, halogen, alkyl, alkoxy and nitro, in the presence of aqueous acetic acid at a temperature in the range of 70-150° C. for a period of 1-5 hrs to yield the compound of formula (3).

10. The process of claim 9 wherein the concentration of aqueous acetic acid is in the range of 50% to 98% solution in water.

11. The process of claim 10 wherein the compound of formula (1) is selected from the group consisting of 1,2-phenylenediamine, 3,4-dimethyl-1,2-phenylenediamine, methyl-1,2-phenylenediamine-4-benzoate and 4-methyl-1,2-phenylenediamine.

12. The process of claim 11 wherein the compound of formula (2) is selected from the group consisting of isatoic anhydride, 6-fluoro isatoic anhydride, and 6-chloro isatoic anhydride.

13. The process of claim 12 wherein the compound of formula (3) is selected from the group consisting of 10,11-dihydro-5H-dibenzo[b,e][1,4]diazepin-11-one; 2-fluoro-10,11-dihydro-5H-dibenzo[b,e][1,4]diazepin-11-one; 2-chloro-10,11-dihydro-5H-dibenzo[b,e][1,4]diazepin-11-one; 8,9-dimethyl-10,11-dihydro-5H-dibenzo[b,e][1,4]diazepin-11-one; methyl 11-oxo-10,11-dihydro-5H-dibenzo[b,e][1,4]diazepin-8-carboxylate and 2-chloro-8-methyl-10,11-dihydro-5H-dibenzo[b,e][1,4]diazepin-11-one.

14. The process of claim 13 wherein the yield of the compound of formula (3) is in the range of 85%-98%.

* * * * *